United States Patent
Schweitzer, Jr. et al.

(10) Patent No.: US 6,850,789 B2
(45) Date of Patent: Feb. 1, 2005

(54) COMBINATION SPO2/TEMPERATURE MEASURING APPARATUS

(75) Inventors: Frederick F. Schweitzer, Jr., Skaneateles, NY (US); Raymond A. Lia, Auburn, NY (US); Robert L. Vivenzio, Auburn, NY (US); Kenneth J. Burdick, Skaneateles, NY (US); Dominick Danna, Syracuse, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 248 days.

(21) Appl. No.: 10/207,532

(22) Filed: Jul. 29, 2002

(65) Prior Publication Data

US 2004/0019293 A1 Jan. 29, 2004

(51) Int. Cl.[7] ................................. A61B 5/00
(52) U.S. Cl. ................. 600/340; 600/549; 600/483
(58) Field of Search ........................... 600/323, 324, 600/325, 339, 340, 344, 549, 481, 483, 500, 502, 519

(56) References Cited

U.S. PATENT DOCUMENTS

| 4,493,564 A | 1/1985 | Epstein |
| 4,890,619 A | 1/1990 | Hatschek |
| 5,213,099 A | 5/1993 | Tripp, Jr. |
| 5,343,869 A | 9/1994 | Pross et al. |
| 5,357,954 A | 10/1994 | Shigezawa et al. |
| 5,634,720 A | 6/1997 | Gallup et al. |
| 5,673,692 A | 10/1997 | Schulze et al. |
| 5,715,816 A | 2/1998 | Mainiero et al. |
| 5,743,261 A | 4/1998 | Mainiero et al. |
| 5,916,153 A * | 6/1999 | Rhea, Jr. .............. 600/339 |
| 6,006,120 A | 12/1999 | Levin |
| D430,812 S | 9/2000 | Levin et al. |
| 6,430,422 B1 | 8/2002 | Kimura |

FOREIGN PATENT DOCUMENTS

| JP | 6233745 | 8/1994 |
| WO | 98/03847 | 1/1998 |
| WO | 00/13575 | 3/2000 |

* cited by examiner

Primary Examiner—Eric F. Winakur
(74) Attorney, Agent, or Firm—Wall Marjama & Billinski LLP

(57) ABSTRACT

A medical diagnostic instrument includes at least one blood oxygen saturation sensor and at least one temperature sensor. The sensors are being capable of measuring blood oxygen saturation and temperature simultaneously after insertion of a probe portion of the instrument relative to a defined body site, such as the axilla, rectum, or sublingual pocket of a patient. At least a portion of the probe portion of the instrument is disposable.

54 Claims, 3 Drawing Sheets

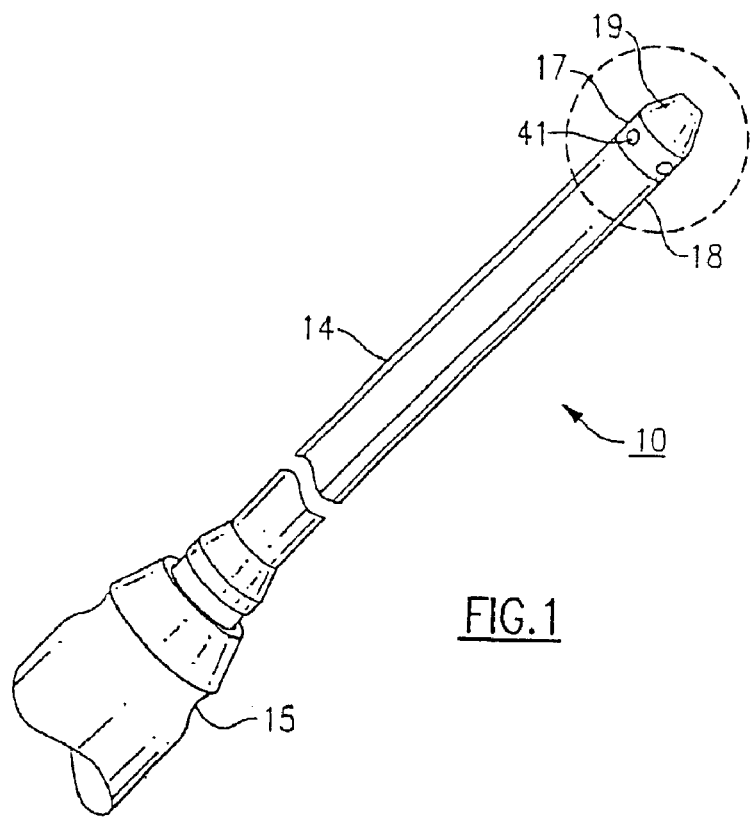
FIG. 1
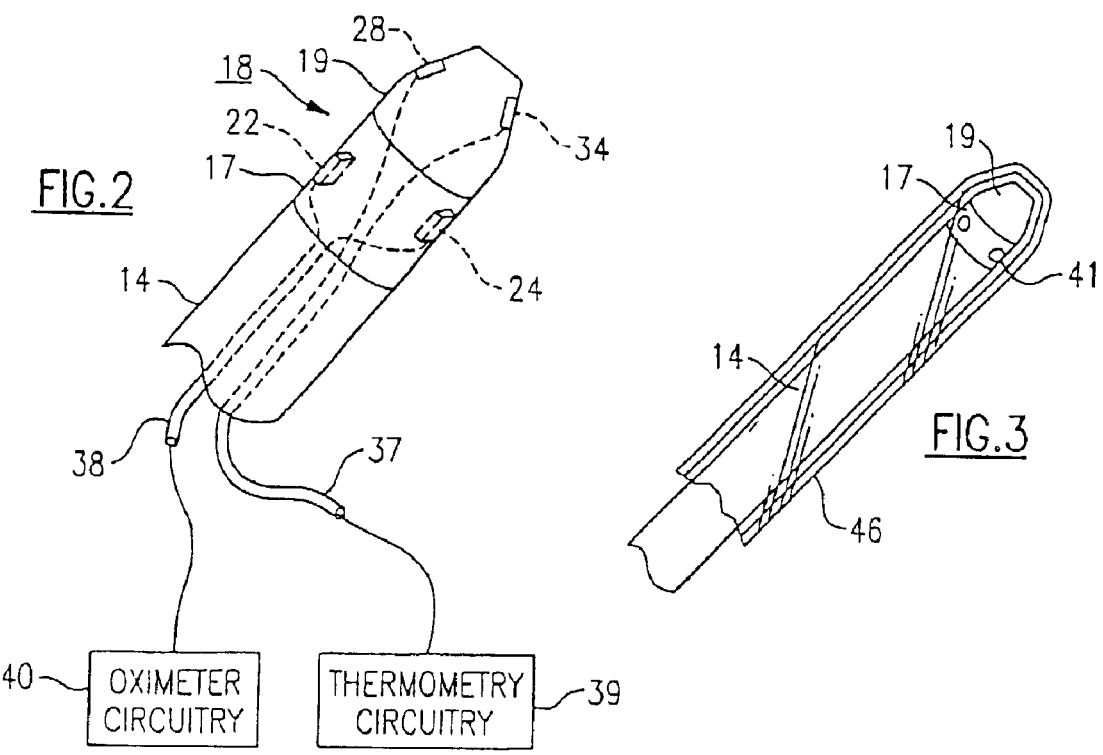
FIG. 2
FIG. 3

COMBINATION SPO2/TEMPERATURE MEASURING APPARATUS

FIELD OF THE INVENTION

The invention relates to the field of medical diagnostic apparatus and in particular to a combination temperature/blood oxygen saturation measuring device that is suitable for use in a number of separate patent body sites, most prominently in the sublingual pocket and axilla.

BACKGROUND OF THE INVENTION

In the prior art of thermometry, it has been determined that predictive or directly measured temperature can be obtained in the sublingual pocket of the human mouth due to the blood supply and vascular tissue found under the tongue. It has also been determined that the arterial blood supplied by the sublingual artery can also provide an environment which is suitable for accurate pulse oximeter readings or measurements.

To date, there are a number of pulse oximeter probes which have been adapted for use with either pulse detection apparatus or thermometers to measure blood oxygen saturation. For example, as described in U.S. Pat. No. 5,673,692 to Schulze et al., a combination device is described including an infrared temperature sensor and a pulse oximeter that can be used within the ear. Other devices have been described which can be used in the esophagus, such as that described by Maniero et al., (U.S. Pat. No. 5,715,816). Though the above devices are useful in obtaining parameter measurements, they are somewhat limited to those specific body sites. There is a need generally found in the field to provide a measuring instrument which can be used to suitably and comfortably provide real time temperature and pulse oximeter measurements in a number of body sites, such as the sublingual pocket, or the axillary area of a patient.

SUMMARY OF THE INVENTION

It is therefore a primary object to overcome the above-noted deficiencies of the prior art.

It is another primary object of the present invention to develop an improved diagnostic instrument which can measure body temperature and saturation blood volume simultaneously in a single instrument and which is useful in at least one and preferably each of the axilla and an oral cavity (sublingual pocket, rectum, etc.) of a patient.

Therefore and according to a preferred aspect of the present invention, there is disclosed a medical diagnostic instrument for measuring at least two patient parameters, said instrument comprising means for measuring the blood oxygen saturation of a patient, and means for measuring the body temperature of the patient, each of said measuring means being capable of measuring each said patient parameter simultaneously and used within a defined body site of a patient, said instrument including a probe portion which is insertable into the body site.

Preferably, the temperature measuring means and the blood oxygen saturation measuring means are each provided in the probe portion of the diagnostic instrument. The temperature measuring means includes at least one thermistor, thermocouple, or other form of temperature sensing element, and at least one heating element which is adjacent the at least one temperature sensing element used to acclimate the at least one temperature sensing element in order to avoid the thermal effects of other portions of the probe portion of the instrument and to hasten overall measurement time.

The pulse oximeter measuring means includes at least one light emitter and light detector pair which are arranged within the probe section of the instrument. According to a preferred embodiment, the portion of the probe which retains the pulse oximeter means can be either wholly or partially constructed from a low thermally conductive material to avoid or isolate any thermal effects caused by heat dissipation of the components of the pulse oximeter means relative to the temperature measuring portion of the instrument. According to another embodiment, the heat generated by the pulse oximeter means can also be used constructively to aid in the heating of the temperature measuring portion of the herein described instrument. According to still another embodiment, at least certain components of the pulse oximeter means can be disposed remotely from the probe, such as in the proximal end thereof, and include optical fibers to transmit light to the body site and receive reflected light from the body site.

In addition, the optical nature of the pulse oximeter means can be used to detect when the probe has actually entered the mouth or other body site of a patent. This detection is very useful for predictive-type thermometers (i.e.; those which provide readings in less than 30 seconds) because knowing the time of probe insertion is very important to the algorithms which are used in the processing software used in these thermometers. The pulse oximetry means can discern human tissue from other materials, therefore the latter capability becomes very robust within the present device.

In addition to blood oxygen saturation, the herein described instrument can also be used to measure the pulse/heart rate of a patient. Preferably, blood oxygen and temperature/pulse data can be readily obtained using the herein-described instrument in an extremely short time period (on or about 10 seconds).

Preferably, the probe portion is at least partially disposable, therefore permitting one-time or single patient use. An optically transparent and disposable sheath covering the probe portion permits reuse of the instrument without cleaning and can also aid in providing a reflective light path for the light emitter/detector of the pulse oximeter portion.

The herein described device can be used advantageously in any oral cavity, including the axilla of a patient, without requiring significant reconfiguration of the instrument. The operation of the instrument is simple for use and implementation for the caregiver with the resulting data being reliable and quickly obtained.

These and other objects, features and advantages will become readily apparent from the following Detailed Description which should be read in conjunction with the accompanying drawings.

BRIEF DESCRIPTION OF THE DRAWINGS

FIG. 1 is a partial perspective view of a medical diagnostic instrument made in accordance with a first embodiment of the present invention;

FIG. 2 is a partial sectioned view of the probe portion of the diagnostic instrument of FIG. 1;

FIG. 3 is a partial top perspective view of the probe portion of the diagnostic instrument of FIGS. 1 and 2;

DETAILED DESCRIPTION

Referring to the FIGS. and in particular to FIGS. 1–3, there is shown a medical diagnostic instrument 10 according to a first embodiment of the present invention. The diagnostic instrument 10 includes an elongated probe portion 14 which is preferably defined as a cylindrical configuration including a distal tip 18 which is sized to permit insertion into an oral cavity (e.g., the sublingual pocket, rectum etc.) of a patient or other definable body site, such as the axilla (also not shown).

Figure 4:
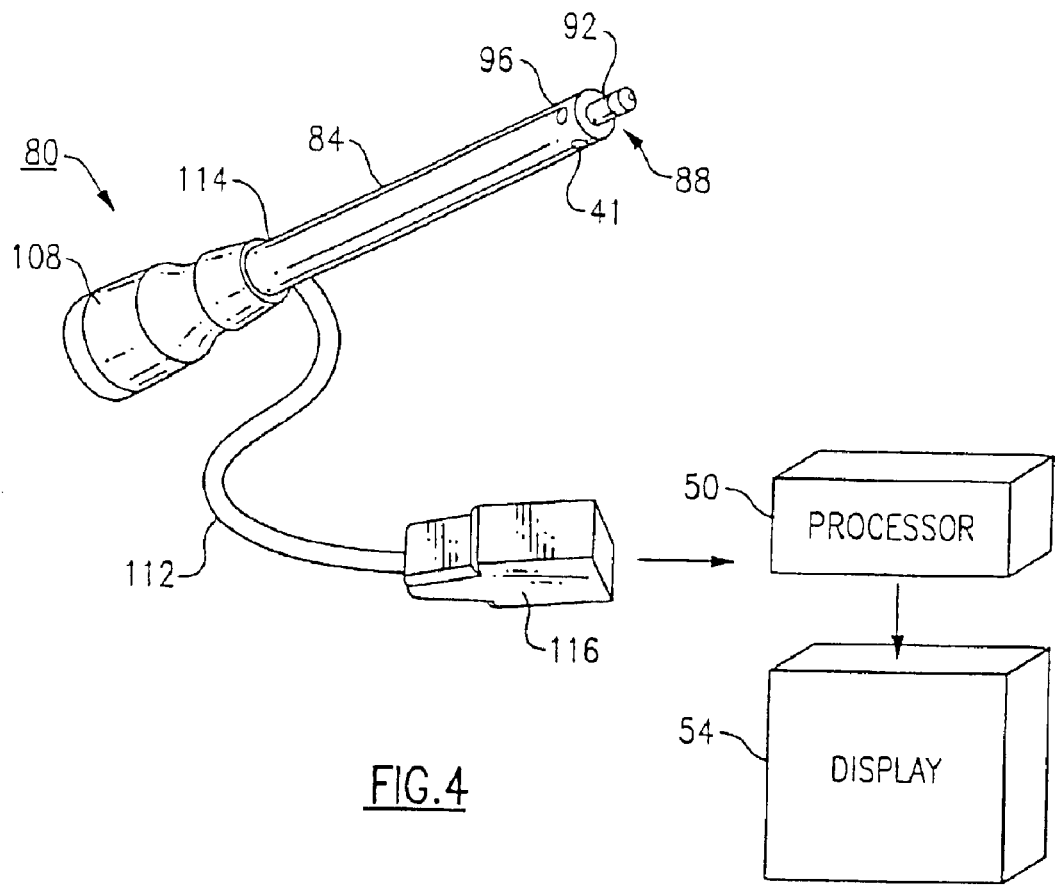
FIG. 4 is a top perspective view of a diagnostic instrument system made in accordance with a second embodiment of the present invention.

The probe portion 14 also includes a proximal end 15 which is tethered by means of a transmission cable to a processor in a manner such as shown in FIG. 4. According to this embodiment, the probe section 14 is essentially hollow and contains a number of components including a temperature sensing portion 19 and a pulse oximeter portion 17, each located adjacently at the distal tip 18.

Referring to FIG. 2, the pulse oximeter portion 17 according to this particular embodiment includes at least one light emitter 22 and at least one light detector 24, each of which are specifically arranged within the probe interior immediately proximal to the temperature sensing portion 19, which is provided at the very distal end of the tip 18. The light emitter(s) 22 comprises preferably at least one miniature LED, such as those manufactured by the Stanley Electric Co., Ltd., and is mounted approximately 180 degrees from the light detector(s) 24 relative to the interior cylindrical wall of the probe portion 14. Circuitry 40 for powering the light emitter and light detector 24 are electrically interconnected through at least one electrical conductor 38 which extends therefrom. This circuitry 40 is as described, for example, in U.S. Pat. Nos. 4,266,554 and 4,621,642; the contents of which are herein incorporated by reference in their entirety. The pulse oximeter portion 17 further includes windows 41 which permit light of at least one predetermined wavelength to be emitted by the light emitter 22 and detected using detector 24. The light emitter 22 and light detector 24 are each powered by circuitry 40 which is tethered thereto through leads 38. The circuitry 40 is connected to a power supply (not shown) to power the light emitter and light detector and to receive detected signals from the detector 24 for processing thereof.

The temperature sensing portion 19 of the herein described instrument 10 includes at least one temperature measuring element or sensor 28, such as a thermistor, which is preferably disposed on the exterior of the distal tip 18 along with an adjacently mounted heating element 34, such as a resistive element. The heating element 34 is used in order to raise the temperature sensing portion 19 to a temperature which closely approaches that of the body site into which the distal tip 18 is inserted through tethered circuitry 39. It should be readily apparent that the choice of temperature sensing elements/sensors and heating elements which can be used in the instrument can easily be varied. For example, at least one thermocouple (not shown) or other form of sensor can utilized for the temperature sensing element. Preferably, the temperature sensing portion 19 of the distal tip 18 is made from a highly thermally conductive material, such as stainless steel or aluminum, which is also biocompatible.

The circuitry 39 used in conjunction with a power supply (not shown) for powering the components of the temperature sensing portion 19 and for processing electrical signals generated as a result of temperature change is connected through at least one electrical conductor or lead 37 extending through the interior of the probe section 14. This circuitry is fairly conventional in design and does not require further discussion herein. Each of the circuitry 39, 40 is shown in this embodiment schematically, wherein the circuitry can reside, for example, in a plug-like module at the end of a transmission cable sheathing the leads 37, 38, such as shown in FIG. 2.

According to the present embodiment, it is preferred that the pulse oximeter portion 17 of the above described instrument be thermally isolated from the temperature sensing portion 19 due to the heat dissipative capacity of the light emitter and detector pair 22, 24. Preferably, the axial section of the probe portion 14 containing the pulse oximeter portion 17 is made from a material, such as polycarbonate or a polyamide, having a low thermal conductivity so as to substantially reduce conduction of additional heat to the temperature sensing portion 19 of the distal tip 18 and which does not interfere with temperature measurement of the body site. Alternately or in combination with the above, the pulse oximeter portion 17 can be located in a proximally adjacent compartment (not shown) separated from the temperature sensing portion 19 by an air gap of a predetermined size. Conversely, however, the heat dissipated by the light emitter and detector pair 22, 24 could be alternately used as a means of providing heat in lieu of or in combination with the heating element 34. To that end, the pulse oximeter portion and temperature sensing portions need not be separated and in fact could be integral with one another as part of the distal tip.

In addition, an optically transparent disposable probe cover or sheath 46, such as described in U.S. Pat. No. 4,757,381, the contents of which being incorporated in its entirety by reference, can be placed in overlaying relation relative to the exterior of the elongated probe portion 14, as shown in FIG. 3. The sheath 46 is used typically in intraoral and similar instruments for health and safety reasons and to prevent fluids from being transferred to the exterior of the instrument 10. In addition, it has been determined for purposes of the present invention, that the optically transparent surface of the sheath 46 also permits and facilitates light transmission and enhances the reflective path between the light emitter(s) 22 and the light detector(s) 24, the probe having windows 41 provided to enable light transmission and reception.

In operation, the disposable sheath 46 is initially placed over the exterior of the elongated probe portion 14 with the distal tip 18 being placed at the body site of interest; in this instance, within the sublingual pocket. The light emitter 22 of the pulse oximeter portion, as activated by the circuitry 40, emits wavelengths of visible and infrared light through the window 41 and onto the vascular tissue within the sublingual pocket, the light being reflected back by the vascular tissue beneath the tongue by the sheath 46 to the window 41 and to the light detector 24. The received signals are then transmitted along the lead 38 to the circuitry 40 and subsequently to a remote processor, 50, such as shown in FIG. 4 which, for example, can contain a power supply. A display 54, also shown only in FIG. 4, connected to the processor 50 by conventional means, can be used to display blood oxygen saturation and/or pulse readings obtained and processed from the pulse oximeter portion 17.

Temperature of the body site is measured simultaneously by heating the distal tip 18, and more particularly the temperature sensing portion 19, using the circuitry 39 and a connected power supply (not shown) to heat the resistive heating element 34 prior to insertion of the instrument 10. This initial heating is required to bring the temperature of the distal tip 18 to a temperature which closely typically approximates that of the body site in order to improve the time required to take a measurement. The temperature readings obtained from the sensing element 28 is transmitted along lead 37 to the temperature circuitry 39 and to the processor 50, FIG. 4. Processed temperature readings can be displayed by the display 54, FIG. 4. Using the above approach, both temperature and pulse/blood oxygen saturation readings can be made in a fairly short period of time (e.g. about 10 seconds). As noted, the heat dissipated by the components of the pulse oximeter portion 17 can selectively be isolated from the temperature sensing portion 19, or combined directly therewith.

The optical nature of the light emitter 22 and detector 24, as well as the devices' ability to discern human tissue from other materials provides another feature in that the time of insertion can be detected. Knowing when the probe encounters the body site is extremely useful for heating control and processing given that the time of insertion is essential to the algorithms which are used by the processing circuitry.

Referring to FIG. 4, an instrument 80 made in accordance with a second embodiment of the invention includes a similarly designed probe portion 84 which is substantially cylindrical in configuration including a distal tip 88 having a temperature sensing portion 92 and a proximally adjacent pulse oximetry portion 96. The latter, as in the preceding, includes an internally disposed light emitter, such as an LED (not shown), and a light detector (not shown). The temperature sensing portion 92 includes a temperature sensing element and preferably a heating element, such as previously shown.

The instrument 80 is sized to be hand-held by a user and includes a proximal handle 108. Transmission cable 112 containing a plurality of electrical conductors or leads (not shown, but similar to those previously shown in FIG. 2) for powering the active components of the temperature sensing portion 92 and the pulse oximetry portion 96 extends from a proximal end 114 of the probe portion 84 to a processor module 116 containing resident circuitry, such as previously shown, incorporated into a plug-like configuration at the end of the cable. The processor module 116 is sized to be fitted to the remote processor 50, which can for example, include a power supply, which is interconnected to a display 54. The processor module 116 and the remote processor 50 permit the signals generated by the light detector and the temperature sensing element to be processed for display as well as power all of the active components of the instrument 80.

Figure 5:
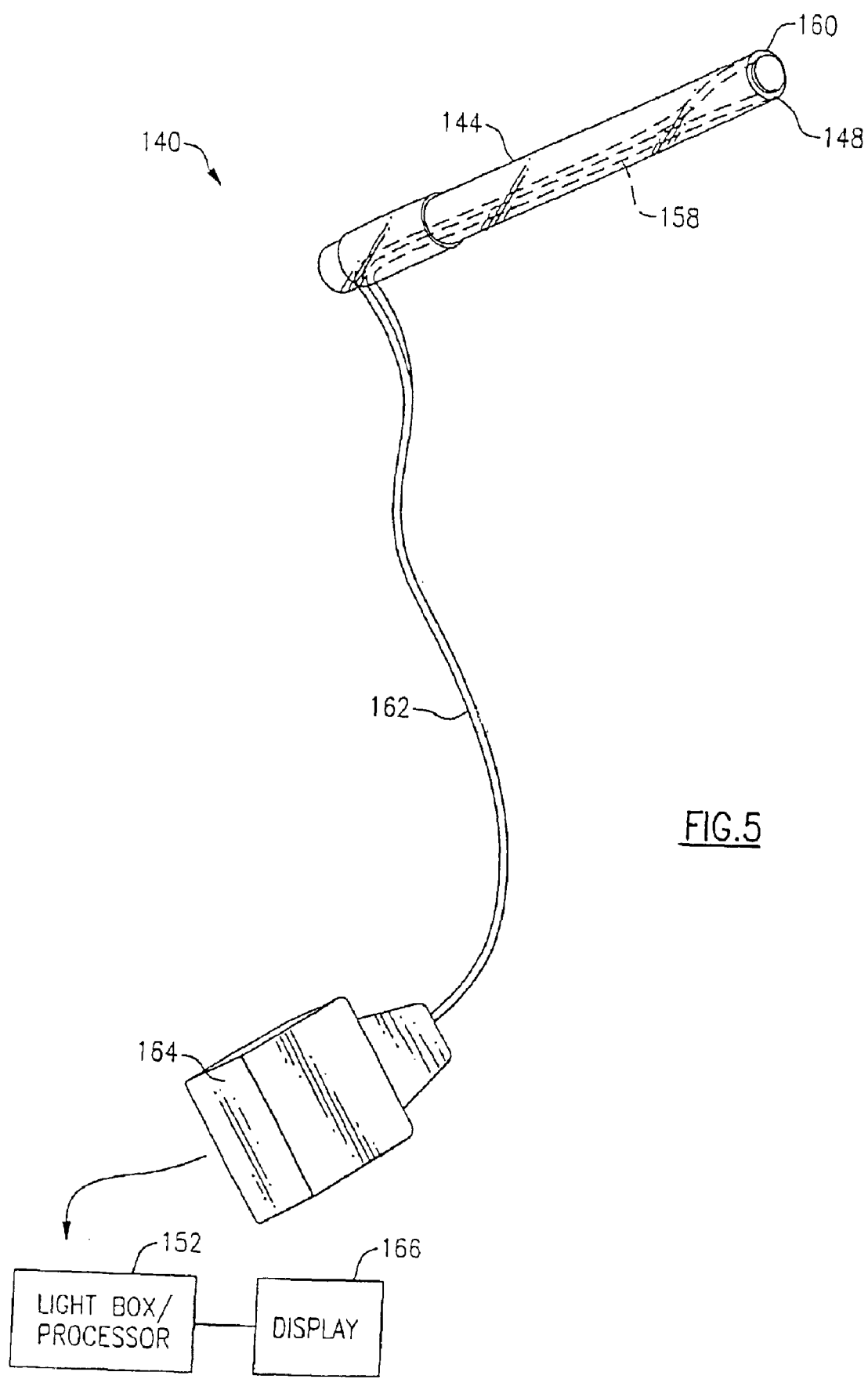
FIG. 5 is a top perspective view of a diagnostic instrument system made in accordance with a third preferred embodiment of the invention.

Referring to FIG. 5, an instrument 140 of similar construction is illustrated with regard to a third embodiment of the invention. The instrument 140 includes a substantially cylindrical probe section 144. According to this embodiment and in lieu of placing a light emitter in the distal tip 148, an LED or other suitable light emitter (not shown) contained in a light box/processor 152. A bundle of optical light transmitting fibers 158 (shown in phantom) are used to convey the light from the light emitter 152 to the distal tip 148 for transmission thereof at a light transmitting end. According to this embodiment, light is transmitted axially through the distal end 148 of the instrument 140, though the orientation of the fibers can be suitably adjusted. Light is transmitted at the body site and reflected therefrom, the reflected light being received and carried by adjacent optical fibers to a light detector, (not shown) which according to this embodiment is also disposed in the light box/processor. Alternately, the light detector(s) can be located in the distal tip 148 and the optical fibers can be located so as to transmit the light from the light emitter through a window, not shown, in a radial fashion from the distal tip of the instrument. The signals received by the light detector can then be carried along the optical fibers along a sheathed transmission cable 162 that is tethered to the instrument 140 and extending to a processor plug module 164 at the end of the cable having suitable processing circuitry which interfaces with and is coupled to the light box/processor 152 and a display 166.

The herein described diagnostic instrument 140 further includes a temperature sensing portion 160, which as in the preceding, includes at least one temperature sensing element and a resistive heater element, each of which are provided at the distal tip 148 of the instrument and preferably at the exterior thereof. Each of the components of the temperature sensing portion 160 as well as the light emitter and detector are powered by a power supply (not shown) such as batteries, a wall transformer or other suitable source such as contained in processor 152 in combination with the circuitry provided in the processor plug-in module 164.

Each of the preceding instruments can be powered automatically by plugging the plug-in module 164 into the processor 152 or by means of a manual switch (not shown) provided on the probe portion or handle of the instrument.

Figure 6:
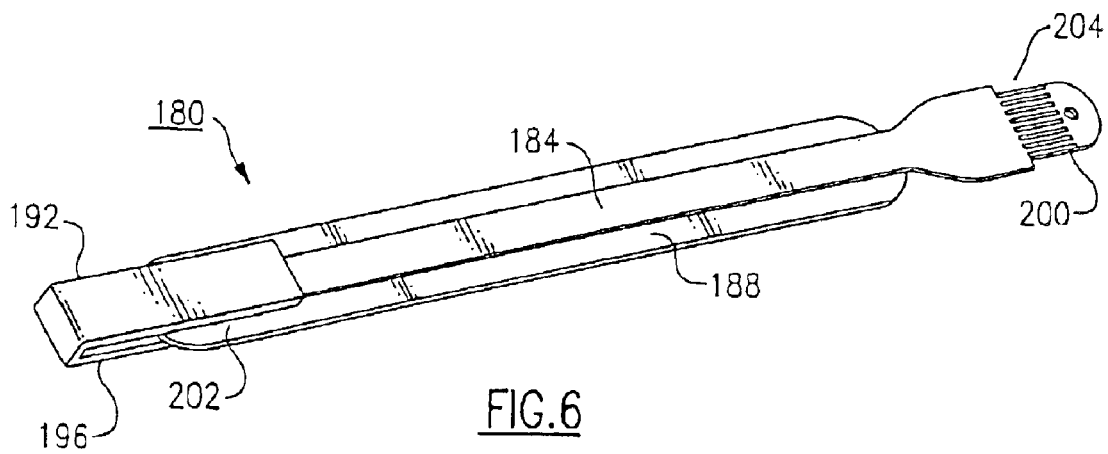
FIG. 6 is a perspective view of a diagnostic instrument system made in accordance with a fourth preferred embodiment of the invention.

It should be readily apparent that other variations and modifications of the herein described instrument are possible other than the cylindrical probe portion previously described. For example and referring to FIG. 6, an instrument 180 in accordance with a fourth embodiment is defined by a planar configuration in which a probe section 184 includes as a relatively thin substrate 188, similar in shape to that of a tongue depressor, and onto which a pulse oximeter portion 192 comprising a light emitter/transmitter and light receiver/sensor pair can be mounted suitably in combination with a temperature sensing portion 202 including a temperature sensing element and heater element respectively, each of the temperature sensing portion and pulse oximeter portions being disposed at a distal end 196. Conductive traces 200 at the opposite or proximal end 204 of the instrument permit connection to a power supply (not shown) and processing circuitry (not shown).

Parts List for FIGS. 1–6
10 instrument
14 probe section
15 proximal end
17 pulse oximeter portion
18 distal tip
19 temperature sensing portion
22 light emitter
24 light detector
28 temperature sensing element
34 heating element
37 electrical conductors or leads
38 electrical conductors or leads
39 circuitry
40 circuitry
41 windows
46 disposable sheath
50 processor
54 display
80 instrument
84 probe portion
88 distal tip
92 temperature sensing portion
96 pulse oximetry portion 108 handle
112 transmission lines
114 proximal end
116 processor module
140 instrument
144 probe portion
148 distal tip
152 light box/processor
158 optical fibers
160 temperature sensing portion
162 transmission cable
164 processor plug module
166 display
180 instrument
184 probe section
188 planar substrate
192 pulse oximeter portion
196 distal end
200 conductive traces
202 temperature sensing portion
204 proximal end

We claim:

1. A medical diagnostic instrument comprising:
a hollow elongate probe portion which is insertable into a body site;
means for measuring the blood oxygen saturation of a patient;
means for measuring the temperature of the patient, each of said measuring means being arranged within said elongate probe portion and capable of measuring simultaneously with the other of said measuring means, said blood oxygen saturation measuring means including at least one light transmitter and at least one light detector and said temperature measuring means including at least one temperature sensing element; and
a transparent sheath sized for covering said probe portion.

2. The instrument of claim 1, wherein said body site is the axilla of a patient into which said elongate probe portion can be inserted.

3. The instrument of claim 1, further including means for measuring the pulse rate of a patient disposed within said elongate probe portion of said instrument.

4. The instrument of claim 1, including display means for displaying at least one of said measured parameters.

5. The instrument of claim 1, wherein said body site is the sublingual pocket of a patient into which said elongate probe portion of said instrument can be inserted.

6. The instrument of claim 1, wherein said body site is the rectum into which said elongate probe portion of said instrument can be inserted.

7. The instrument of claim 1, wherein said temperature sensing element is disposed at a distal end thereof and in which said at least one light transmitter and at least one light detector are arranged adjacent to said temperature sensing element.

8. The instrument of claim 7, wherein said at least one light transmitter and light detector includes at least one optical fiber disposed in the distal end of said probe portion, said at least one optical fiber being capable of at least one of transmitting and receiving light relative to a said body site.

9. The instrument of claim 1, including at least one light transmitter and at least one light sensor disposed in relation to at least one optical fiber disposed in the distal end of said hollow elongate probe portion, said at least one optical fiber being capable of transmitting and receiving light relative to said body site, said at least one light transmitter and said at least one light sensor being disposed remotely from the distal end of said probe portion.

10. The instrument of claim 1, wherein said temperature measuring means includes at least one thermistor and resistance measuring means connected electrically to said at least one thermistor, wherein said at least one thermistor is disposed in a distal end of said probe portion.

11. The instrument of claim 1, wherein said temperature measuring means includes at least one thermocouple.

12. The instrument of claim 1, wherein said probe portion includes a substrate having said blood oxygen saturation means and said temperature measuring means disposed thereupon.

13. The instrument of claim 1, wherein said temperature measuring means includes at least one heater element disposed in relation to said at least one temperature sensing element.

14. The instrument of claim 1, wherein said blood oxygen saturation measuring means includes a pulse oximeter portion including said at least one light transmitter for transmitting light at said body site and said at least one light detector for detecting light reflected from said body site, said at least one light transmitter and said at least one light detector being arranged such that heat generated from said pulse oximeter portion is isolated from said temperature measuring means.

15. An instrument as recited in claim 1, wherein said transparent sheath provides a reflective path for said at least one of said at least one light transmitter and at least one light detector.

16. The instrument of claim 1, wherein said blood oxygen saturation measuring means includes a pulse oximeter portion, said pulse oximeter portion including said at least one light transmitter for transmitting light at said body site and said at least one light detector for detecting light reflected from said body site, said at least one light transmitter and said at least one light detector being arranged such that heat generated from said pulse oximeter portion can be used to heat the temperature sensing element to a predetermined temperature.

17. The instrument of claim 1, wherein the at least one light transmitter and at least one light detector of said blood oxygen saturation measuring means permits a user to detect the time said instrument is initially inserted in relation to said body site.

18. The instrument of claim 17, wherein said body site is the sublingual pocket into which said elongate probe portion can be inserted.

19. A medical diagnostic instrument comprising:
a hollow elongate probe portion which is insertable into a body site;
means for measuring the blood oxygen saturation of a patient;
means for measuring the temperature of the patient, each of said measuring means being arranged within said elongate probe portion and capable of measuring simultaneously with the other of said measuring means, wherein said temperature measuring means includes at least one temperature sensing element and at least one heater element disposed in relation to said at least one temperature sensing element.

20. The instrument of claim 19, wherein said body site is the axilla of a patient into which said hollow elongate probe portion can be inserted.

21. The instrument of claim 19, further including means for measuring the pulse rate of a patient disposed within said hollow elongate probe portion of said instrument.

22. The instrument of claim 21, wherein said blood oxygen saturation measuring means permits a user to detect the time said elongate probe portion is initially inserted in relation to said body site.

23. The instrument of claim 22, wherein said body site is the sublingual pocket into which the elongate probe portion of said instrument can be inserted.

24. The instrument of claim 19, wherein said blood oxygen saturation measuring means includes at least one light transmitter and at least one light detector.

25. The instrument of claim 24, wherein said temperature sensing element is disposed at a distal end thereof and in which said at least one light transmitter and at least one light detector are arranged adjacent to said temperature sensing element.

26. The instrument of claim 25, wherein said at least one light transmitter and said at least one light detector includes at least one optical fiber disposed in the distal end of said probe portion, said at least one optical fiber being capable of at least one of transmitting and receiving light relative to a said body site.

27. The instrument of claim 26, including at least one light transmitter and one light sensor disposed in relation to said at least one optical fiber remotely from the distal end of said probe portion.

28. An instrument as recited in claim 24, including a transparent sheath sized for covering said elongate probe portion.

29. An instrument as recited in claim 28, wherein said transparent sheath provides a reflective path for said at least one of said at least one light emitter and at least one light detector.

30. An instrument as recited in claim 28, wherein said transparent sheath is disposable.

31. The instrument of claim 19, including display means for displaying at least one of said measured parameters.

32. The instrument of claim 19, wherein said body site is the sublingual pocket of a patient into which said elongate probe portion of said instrument can be inserted.

33. The instrument claim 19, wherein said body site is the rectum into which said elongate probe portion of said instrument can be inserted.

34. The instrument of claim 19, wherein said temperature measuring means includes at least one thermistor and resistance measuring means connected electrically to said at least one thermistor, wherein said at least one thermistor is disposed in a distal end of said elongate probe portion.

35. The instrument of claim 19, wherein said temperature measuring means includes at least one thermocouple.

36. The instrument of claim 19, wherein said probe portion includes a substrate having said blood oxygen saturation means and said temperature measuring means disposed thereupon.

37. The instrument of claim 19, wherein said blood oxygen saturation volume measuring means includes a pulse oximeter portion including at least one light emitter for transmitting light at a said body site and at least one light detector for detecting light reflected from said body site, said at least one light emitter and said at least one light detector being arranged such that heat generated from said pulse oximeter portion is isolated from said temperature measuring means.

38. The instrument of claim 19, wherein said blood oxygen saturation measuring means includes a pulse oximeter portion, said pulse oximeter portion including at least one light transmitter for transmitting light at said body site and at least one light detector for detecting light reflected from said body site, said at least one light transmitter and said at least one light detector being arranged such that heat generated from said pulse oximeter portion can be used to heat the temperature sensing element to a predetermined temperature.

39. A medical diagnostic instrument comprising:
a hollow elongate probe portion which is insertable into a body site;
means for measuring the blood oxygen saturation of a patient; and
means for measuring the temperature of the patient, each of said measuring means being arranged within said elongate probe portion and capable of measuring simultaneously with the other of said measuring means and used within a defined body site of a patient, wherein said blood oxygen saturation measuring means includes a pulse oximeter portion, said pulse oximeter portion including at least one light transmitter for transmitting light at said body site and at least one light detector for detecting light reflected from said body site, said at least one light transmitter and said at least one light detector being arranged such that heat generated from said pulse oximeter portion can be used to heat the temperature measuring means to a predetermined temperature.

40. The instrument of claim 39, wherein said body site is the axilla of a patient into which said hollow elongate probe portion can be inserted.

41. The instrument of claim 39, further including means for measuring the pulse rate of a patient disposed within said elongate probe portion of said instrument.

42. The instrument of claim 39, including display means for displaying at least one of said measured parameters.

43. The instrument of claim 39, wherein said body site is the sublingual pocket of a patient into which said elongate probe portion of said instrument can be inserted.

44. The instrument of claim 39, wherein said body site is the rectum into which said elongate probe portion of said instrument can be inserted.

45. The instrument of claim 39, wherein said temperature measuring means includes at least one temperature sensing element disposed at a distal end of said instrument and in which said at least one light transmitter and said at least one light detector are arranged adjacent to said at least one temperature sensing element.

46. The instrument of claim 45, wherein said at least one light transmitter and light receiver includes at least one optical fiber disposed in the distal end of said elongate probe portion, said at least one optical fiber being capable of at least one of transmitting and receiving light relative to said body site.

47. The instrument of claim 39, wherein said temperature measuring means includes at least one thermistor and resistance measuring means connected electrically to said at least one thermistor, wherein said at least one thermistor is disposed in a distal end of said probe portion.

48. The instrument of claim 39, wherein said temperature measuring means includes at least one thermocouple.

49. The instrument of claim 39, said probe portion includes a substrate having said blood oxygen saturation means and said temperature measuring means disposed thereupon.

50. An instrument as recited in claim 39, including a transparent sheath sized for covering said probe portion.

51. An instrument as recited in claim 50, wherein said transparent sheath provides a reflective path for said at least one of said at least one light transmitter and at least one light detector.

52. The instrument of claim 39, wherein the at least one light detector and at least one light transmitter of said blood oxygen saturation measuring means permits a user to detect the time said instrument is initially inserted in relation to said body site.

53. The instrument of claim 52, wherein said body site is the sublingual pocket.

54. A medical diagnostic instrument comprising:

a hollow elongate probe portion which is insertable into a body site;

means for measuring the blood oxygen saturation of a patient; and means for measuring the temperature of the patient, each of said measuring means being arranged within said elongate probe portion and capable of measuring simultaneously with the other of said measuring means and used within a defined body site of a patient, wherein said blood oxygen saturation measuring means includes a pulse oximeter portion including said at least one light transmitter for transmitting light at said body site and said at least one light detector for detecting light reflected from said body site, said at least one light transmitter and said at least one light detector being arranged such that heat generated from said pulse oximeter portion is isolated from said temperature measuring means.

* * * * *